United States Patent [19]

Riehm

[11] 4,139,571
[45] Feb. 13, 1979

[54] $C_8$ ALKYL AROMATIC HYDROCARBON ISOMERIZATION BY RECYCLING BENZENE AND TOLUENE

[75] Inventor: Roger A. Riehm, Media, Pa.

[73] Assignee: Atlantic Richfield Company, Philadelphia, Pa.

[21] Appl. No.: 833,218

[22] Filed: Sep. 14, 1977

[51] Int. Cl.² .................... C07C 15/06; C07C 15/08; C07C 15/24
[52] U.S. Cl. .......................... 260/668 A; 260/674 A
[58] Field of Search ................................... 260/668 A

[56] References Cited
U.S. PATENT DOCUMENTS 3,553,276   1/1971   Berger et al. .................... 260/668 A Primary Examiner—Veronica O'Keefe
Attorney, Agent, or Firm—Frank J. Uxa

[57] ABSTRACT

An improved $C_8$ alkyl aromatic hydrocarbon isomerization process comprising the steps of (1) contacting the feedstock with an isomerization catalytic composite in the presence of hydrogen at isomerization conditions to isomerize at least a portion of the $C_8$ alkyl aromatic hydrocarbons and to produce an effluent; (2) separating the effluent to form a hydrogen-rich gaseous fraction, a first hydrocarbon-rich fraction containing toluene and having a lower average molecular weight relative to $C_8$ alkyl aromatic content, and a second fraction enriched in $C_8$ alkyl aromatic content relative to the effluent; provided that at least a portion of the first hydrocarbon-rich fraction is subjected to the contacting of step (1); and (3) recovering at least one $C_8$ alkyl aromatic product from the second fraction. Improved yields of specific desired $C_8$ hydrocarbon isomers and more efficient and complete $C_8$ alkyl aromatic isomerization are among the benefits obtained.

16 Claims, No Drawings

$C_8$ ALKYL AROMATIC HYDROCARBON ISOMERIZATION BY RECYCLING BENZENE AND TOLUENE

This invention relates to a $C_8$ alkyl aromatic isomerization process. More particularly, this invention relates to an improved $C_8$ alkyl aromatic isomerization process wherein by-products having a lower molecular weight than $C_8$ alkyl aromatics are produced.

Processes for the production of various $C_8$ alkyl isomers are of importance within the petroleum and petrochemical industries. This interest stems from the demand for specific isomers, in particular, paraxylene and orthoxylene. Thus, a mixed $C_8$ alkyl aromatic stream may be fed to one or more separation steps or units, e.g., crystallization, adsorption, superfractionation and the like, for separation of one or more specific $C_8$ alkyl aromatic isomers. The remaining $C_8$ alkyl aromatic material is often fed to an isomerization reaction zone wherein the concentration of the desired isomer or isomers is replenished. The effluent, or at least a portion of the effluent, from the isomerization reaction zone is then fed to the separation unit for recovery of the desired isomer or isomers.

In one particular $C_8$ alkyl aromatic isomerization process, the isomerization is commonly affected by contacting the hydrocarbon in admixture with hydrogen at isomerization conditions with a dual function catalyst possessing both hydrogenation and cracking activities thereby effecting the desired isomerization reaction. By contacting the $C_8$ alkyl aromatic with the catalyst at isomerization conditions, $C_8$ naphthalenes, toluene and $C_9+$ aromatics, among other by-products, are often produced. It has been found that such $C_8$ naphthenes are beneficially maintained in the $C_8$ alkyl aromatic stream sent to the separation zone and then recycled back to the isomerization zone to improve the yield of the specific or desired $C_8$ alkyl aromatic isomer. A number of patents have disclosed processing schemes to take advantage of the beneficial effects of recycling $C_8$ naphthenes to a $C_8$ alkyl aromatic isomerization zone. Among these patents are U.S. Pat. Nos. 3,538,173 and 3,553,276.

Although many prior art processes have talked in terms of providing improved yields of the specific or desired alkyl aromatic isomer, it would be clearly advantageous to provide still further improvement in $C_8$ alkyl aromatic isomer yields.

Therefore, one of the objects of the present invention is to provide an improved process for isomerizing a $C_8$ alkyl aromatic hydrocarbon-containing feedstock.

Another object of the present invention is to provide an improved $C_8$ alkyl aromatic isomerization process wherein at least a portion of the $C_8$ naphthenes produced in the isomerization zone is more efficiently recycled to the isomerization zone.

A still further object of the present invention is to provide a $C_8$ alkyl aromatic isomerization process wherein improved yields of at least one of the $C_8$ alkyl aromatic isomers is obtained. Other objects and advantages of the present invention will become apparent hereinafter.

The present invention involves a process for isomerizing a $C_8$ alkyl aromatic hydrocarbon-containing feedstock. This process comprises the steps of (1) contacting the feedstock with an isomerization catalytic composite in the presence of hydrogen at isomerization conditions to isomerize at least a portion of the $C_8$ alkyl aromatic hydrocarbons and to produce an effluent; (2) separating the effluent to form a hydrogen-rich gaseous fraction, a first hydrocarbon-rich fraction containing toluene and having a lower average molecular weight relative to $C_8$ alkyl aromatic content, and a second fraction enriched in $C_8$ alkyl aromatic content relative to the effluent; and (3) recovering at least one $C_8$ alkyl aromatic product from the second fraction. The present improvement comprises subjecting at least a portion of the first hydrocarbon-rich fraction to the contacting of step (1). In other words, one embodiment of the present invention involves recycling at least a portion of the first hydrocarbon-rich fraction to the contacting of step (1). The improved process described above has surprisingly been found to provide improved yields of specific or desired $C_8$ alkyl aromatic hydrocarbon isomers and more efficient and complete $C_8$ alkyl aromatic isomerization.

Among the reactions which often occur in the isomerization zone of the present process are the production of $C_8$ naphthenes and toluene. These naphthenes are produced, for example, by the hydrogenation of the $C_8$ alkyl aromatics, some naphthenes being subsequently isomerized. Toluene is often produced by disproportionation of $C_8$ alkyl aromatics, as well as other cracking-type reactions.

In one preferred embodiment, the process of the present invention is as follows. A hydrocarbon feedstock comprising $C_8$ alkyl aromatic hydrocarbons, i.e., paraxylene, orthoxylene, metaxylene and ethylbenzene, in a non-equilibrium mixture is contacted with a catalytic composite in the presence of hydrogen at isomerization conditions in at least one reaction zone. The reaction zone effluent is passed to a gas separation zone, e.g., flash drum and the like, wherein a hydrogen-rich gaseous fraction is removed from the effluent. At least a portion of this hydrogen-rich gaseous fraction is preferably recycled back to the isomerization zone to make-up at least a portion of the hydrogen in the presence of which the isomerization reaction takes place. The remainder of the effluent from this gas separation zone proceeds to a second separation zone, e.g., distillation tower and the like, wherein a first hydrocarbon-rich fraction containing toluene, e.g., which is produced in the isomerization reaction zone, and having a lower average molecular weight relative to $C_8$ alkyl aromatics is recovered. The remainder of the effluent, which comprises a second fraction enriched in $C_8$ alkyl aromatic content relative to the total isomerization zone reactor effluent is sent to further separation zones, e.g., distillation, crystallization, adsorption, superfractionation and the like, for recovery of at least one desired $C_8$ alkyl aromatic isomer product. Preferably, at least a portion of the $C_9$ and heavier hydrocarbon material, e.g., produced in the isomerization zone, is removed from the effluent. At least a portion of the $C_8$ alkyl aromatic hydrocarbons remaining after recovery of the desired isomer product or products is preferably recycled to the isomerization zone for further isomerization. At least a portion of the first hydrocarbon-rich fraction is sent to the isomerization reaction zone. By sending at least a portion of the first hydrocarbon-rich fraction to the isomerization reaction zone, improved yields of specific or desired $C_8$ alkyl aromatic hydrocarbon isomers are obtained as well as more efficient and complete $C_8$ alkyl aromatic isomerization. In one embodiment, the first hydrocarbon-rich fraction also contains $C_8$ naphthenes.

In one specific embodiment, the remainder of the isomerization reaction zone effluent from the gas separation zone is fed to a distillation tower system, e.g., including a column or columns, and associated equipment such as reboilers, condensors, coolers, product collection zones, pumps and the like, wherein lower boiling materials are concentrated in the overhead product from such tower. The overhead product of this tower may, for example, by controlling the tower operating pressure, be maintained totally or substantially totally in the liquid phase. However, in a preferred embodiment, the distillation tower is controlled or operated so that a portion of the overhead product leaves the system as a gaseous material. In this embodiment, at least a portion of the liquid overhead product of this tower is routed to the isomerization zone. In an additional embodiment, the first hydrocarbon-rich fraction which is at least partially routed to the isomerization zone may be taken as a side stream product from this distillation tower. In any event, the first hydrocarbon-rich fraction may be characterized as containing toluene, and possibly $C_8$ naphthenes, and having a lower average molecular weight relative to $C_8$ alkyl aromatics. In a preferred embodiment, this first hydrocarbon-rich fraction is substantially free of $C_8$ alkyl aromatic hydrocarbons, e.g., contains less than about 5%, more preferably less than about 1%, by weight of $C_8$ alkyl aromatics.

The first hydrocarbon-rich fraction may further contain $C_1$ to $C_8$ paraffins such as methane, ethane, propane, butane, pentane, hexane, heptane, and octane having various structural configurations; $C_5$, $C_6$ and $C_7$ naphthenes and benzene. Preferred component concentrations in the first hydrocarbon-rich fraction are as follows:

0% to about 40% by weight $C_1$ to $C_4$ components,
0% to about 40% by weight $C_5$ to $C_8$ paraffins,
about 1% to about 20% by weight of $C_5$ to $C_7$ naphthenes,
0% to about 50% by weight $C_8$ naphthenes,
about 1% to about 20% by weight benzene, and
about 3% to about 70% by weight of toluene.

Preferably, the separation zone, e.g., distillation tower or towers, which produces the first hydrocarbon-rich fraction is designed so that a substantial portion of the toluene and $C_8$ naphthenes in the feed to this separation zone, e.g., in the isomerization zone feedstock and produced in the isomerization reaction zone, remains with the material which is sent to further processing, e.g., the bottoms product from the distillation tower. Thus, the amount of toluene in the first hydrocarbon-rich fraction is preferably a portion, more preferably more than about 10% and still more preferably more than about 20%, of the total toluene in the feed to this separation zone. The amount of $C_8$ naphthenes in the first hydrocarbon-rich fraction, if any, is preferably a portion, more preferably less than about 90% and still more preferably less than about 80%, of the total $C_8$ naphthenes in the feed to this separation zone. Preferably, only a portion, e.g., at least about 30%, more preferably at least about 40% and still more preferably, at least about 50% by weight of the first hydrocarbon-rich fraction is routed to the isomerization reaction zone. A portion of this material is preferably removed from the process in order to control the level of toluene and/or lighter components in the reaction zone to an economically reasonable level. Since, in a preferred embodiment, this first hydrocarbon-rich fraction also contains $C_8$ naphthenes, $C_8$ naphthenes are removed from the process by removing a portion of the first hydrocarbon-rich fraction. This loss in $C_8$ naphthenes in the first hydrocarbon-rich fraction detrimentally affects the yields of specific desired $C_8$ alkyl aromatic isomers and, therefore, should be minimized, e.g., as described above.

The $C_8$ naphthenes include various alkylcyclopentanes and alkylcyclohexanes such as 1,1,3-trimethylcyclopentane, 1,1,2-trimethylcyclopentane, the 1,2,4-trimethylcyclopentanes, the 1,2,3-trimethylcyclopentanes, 1,1-dimethylcyclohexane, 1,4-dimethylcyclohexane, the methyl-ethylcyclopentanes, etc. It is advantageous to recycle at least a portion of these naphthenic hydrocarbons present in the isomerization zone effluent back to the isomerization reactor thereby minimizing aromatic hydrocarbon losses to naphthenes, since it appears that these naphthenes exist in equilibrium with the $C_8$ alkyl aromatics.

The present process involves at least one isomerization catalytic composite. Such catalysts include at least one hydrogenation-dehydrogenation component, preferably selected from the group consisting of Group VI metal components, Group VII metal components, Group VIII metal components and mixtures thereof. These metallic components are usually combined with, e.g., impregnated on, a carrier such as at least one acidic inorganic oxide, e.g., alumina, silica-alumina and the like, the faujasites, mordenite, etc., or various combinations thereof, preferably in an amount, calculated on an elemental basis, of about 0.05% to about 30% by weight of the catalyst composite. In addition, the catalysts may contain small amounts, e.g., about 0.1% to about 5.0% by weight of the catalyst, of halogen such as chlorine and/or fluorine, to enhance the catalytic benefit of the catalyst or, even further, such halogens may be continuously passed to the isomerization reaction zone in admixture with the hydrogen and/or hydrocarbon feedstock.

The preferred catalytic materials used in this invention include crystalline aluminosilicates, of either natural or synthetic origin, having an ordered internal structure. These materials are possessed of high surface area per gram and are microporous. The ordered structure gives rise to a definite pore size, related to the structural nature of the ordered internal structure. Several forms are commercially available. For example, a 5A material indicates a material of A structure and a pore size of about 5Å diameter. A 13X material is one of X faujasite structure and 10–13Å pore diameter, and so on. There are also known materials of Y faujasite structure, and others. Many of these materials may be converted to the H or acid form, wherein a hydrogen occupies the cation site. For example, such a conversion may be had with many such materials by ion-exchange with an ammonium ion followed by heating to drive off $NH_3$, or by controlled acid leaching. In general, the H form is more stable in materials having higher Si/Al ratios, such as about 2.5/1 and above. The aluminosilicate concentration is preferably in the range of about 1% to about 75%, more preferably about 5% to about 50%, by weight of the total isomerization catalytic composite.

One material having substantial $C_8$ alkyl aromatic isomerization catalytic activity is H mordenite. Mordenite is a material occuring naturally as the hydrated sodium salt corresponding to:

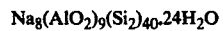

$Na_8(AlO_2)_9(Si_2)_{40}\cdot24H_2O$

This mordenite material may be leached with dilute hydrochloric acid to arrive at an H or acid form. Preferably, the mordenite material useful in the present invention contains more than about 50 percent in the acid form.

Another type of high activity isomerization catalyst may be prepared by using conventional 13X molecular sieve, e.g., such as is described in U.S. Pat. No. 2,882,244. This material may be base exchanged with a solution of rare-earth chlorides (containing 4 percent of $RECl_3.6H_2O$) at about 180°–200° F. to remove sodium ions from the aluminosilicate complex and replace at least some of them with the chemical equivalent of rare-earth ions. After washing free of soluble material and drying, there is produced an REX aluminosilicate containing about 1.0–1.5 percent (wt.) of sodium and about 20 to 30 percent (wt.) of rare earth ions calculated as $RE_2O_3$.

Materials incorporating both metal base exchange and an ammonia base exchange may be obtained by treating simultaneously or serially with metal salts and ammonia, followed by heating, to get metal-hydrogen forms of the crystalline aluminosilicate.

Similar preparations having isomerization catalytic activity may include a variety of crystalline aluminosilicates, such as Y faujasites, gmelinite, chabazite, and the like. For a fuller discussion of the nature of aluminosilicates and their method of preparation attention is also directed to U.S. Pat. No. 3,033,778 to Frilette, and U.S. Pat. No. 3,013,989 to Freeman.

The preferred aluminosilicate-containing catalysts may be varied within wide limits as to aluminosilicate employed, cation character and concentration, and added components incorporated by precipitation, ion exchange, adsorption and the like. Particularly important variables are silica to alumina ratio, pore diameter and spatial arrangement of cations. The cations may be protons (acid) derived by base exchange with solutions of acids or ammonium salts, the ammonium ion decomposing on heating to leave a proton. Polyvalent metals may be supplied as cations, as such or as spacing or stabilizing agents in acid alumino-silicates for stabilization. In addition to the rare-earth metals mentioned above, other suitable cations for exchange in the aluminosilicates include, for example, magnesium, calcium, manganese, cobalt, zinc, silver and nickel.

The preferred crystalline aluminosilicates are the hydrogen and/or polyvalent metal forms of synthetically prepared faujasite and mordenite, particularly, mordenite having an effective diameter of about 6 angstrom units (Å) and a mole ratio of silica to alumina of about 6 to about 15, and more particularly, the hydrogen form of mordenite. A particularly preferred crystalline aluminosilicate is acid-extracted mordenite having an $SiO_2/AL_2O_3$ ratio above about 10. One method of forming this material involves subjecting the ordinary form of mordenite having a $SiO_2/Al_2O_3$ of about 9 to 10 to the action of a strong acid such as hydrochloric acid, sulfuric acid, hydrofluoric acid and the like, at conditions effecting the removal or extraction of at least a portion of the aluminum from the mordenite. Typically, this procedure can be used to obtain mordenite having a $SiO_2/Al_2O_3$ ratio of about 11 or more.

One preferred class of crystalline aluminosilicates useful in the present invention are those materials in which hydrogen, polyvalent metals and mixtures thereof occupy at least about 50%, and more preferably, at least about 90%, of the cation positions of the aluminosilicate structure.

The presently useful isomerization catalytic composites preferably include at least one platinum group metal component. In addition, in some cases, the composite may contain a rhenium component. It is intended to include as a platinum group metals, platinum, palladium, ruthenium, iridium, rhodium and osmium. The platinum group metallic component, such as platinum or palladium, may exist within the final catalytic composite as a compound such as an oxide, sulfide, halide, etc., or as an elemental metal. Generally, the amount of the platinum group metallic component present in the final catalyst is small compared to the quantities of the other components combined therewith. In fact, the platinum group metallic component preferably comprises about 0.02% to about 3.0% by weight of the final catalytic composite, calculated on an elemental basis. Excellent results are obtained when the catalyst contains about 0.2 percent to about 1.0 percent by weight of the platinum group metal.

The catalyst metallic components, e.g., platinum group metallic component, may be incorporated in the catalytic composite in any suitable manner such as coprecipitation or cogellation with the carrier material, ion-exchange with the carrier material, or impregnation either before, during or after incorporation of the aluminosilicate component into the carrier material and either after or before calcination of the carrier material, etc. One preferred method of incorporating the platinum group metal component involves the utilization of water soluble compounds of the platinum group metals with which the carrier material is combined by an impregnation technique. Thus, the platinum group metal may be added to the carrier material by co-mingling the latter with an aqueous solution of chloroplatinic acid. Other water-soluble compounds of platinum may be employed as impregnation solutions and include ammonium chloroplatinate, platinum chloride, dinitro diamino platinum, etc. In one preferred embodiment, the platinum group metal is incorporated, e.g., by impregnation, into the carrier material prior to the alumino silicate being added. In this embodiment, the crystalline aluminosilicate component of the final catalyst is preferably substantially free of platinum group metal. In another preferred embodiment, the carrier material is impregnated after it has been calcined in order to minimize the risk of washing away the valuable platinum metal compounds. However, in some cases, it may be advantageous to impregnate the carrier or support when it is in a gelled state. Following the impregnation, the resulting impregnated support is dried. Additional components, e.g., crystalline aluminosilicates, if any, can be incorporated into the impregnated carrier material using conventional techniques. The presently useful catalysts may be macroformed into particles using conventional techniques such as extrusion, tabletting, spheroidizing and the like. These catalysts are also subjected to high temperature calcination, preferably at temperatures of about 600° F. to about 1500° F. for a period of time in the range of about 0.5 hours to about 20 hours or more.

In one embodiment, the presently useful catalysts include a rhenium component. This component may be present as an elemental metal, as a chemical compound, such as the oxide, sulfide, halide, or in a physical or chemical association with the carrier material and/or the other components of the catalyst. Generally, the rhenium component is utilized in an amount sufficient to result in a final catalytic composite containing about 0.02 to about 1.0 wt. percent rhenium, calculated as an elemental metal. The rhenium component may be incorporated in the catalytic composite in any suitable manner and at any stage in the preparation of the catalyst. One preferred procedure for incorporating the rhenium component involves the impregnation of the carrier material either before, during, or after the other components referred to above are added. The impregnation solution can, in some cases, be an aqueous solution of a suitable rhenium salt such as ammonium perrhenate, sodium perrhenate, potassium perrhenate and the like salts. In addition, aqueous solutions of rhenium halides such as the chlorides may be used if desired; however, the preferred impregnation solution is an aqueous solution of perrhenic acid. The rhenium component can be impregnated either prior to, simultaneously with, or after the platinum group metallic component is added to the carrier material. However, best results are achieved when the rhenium component is impregnated simultaneously with the platinum group metallic component.

Typical reaction conditions utilized in the present process include temperatures of about 50° F. to about 1200° F., preferably about 400° F. to about 1000° F., weight hourly space velocities (weight of hyrocarbons passed per hour per weight of catalyst) of about 0.1 to about 40, preferably about 0.5 to about 8, reaction pressures of about atmospheric to about 100 atmospheres or more, preferably about 5 atmospheres to about 50 atmospheres, and hydrogen to $C_8$ alkyl aromatic hydrocarbon mole ratios of about 0.5:1 to about 25:1 or more, preferably about 3:1 to about 15:1. In a preferred embodiment, the reactants in the isomerization zone are substantially vaporous.

The method of recovering the $C_8$ isomer product from the reactor effluent is, in part, a function of the particular isomer desired. For example, if orthoxylene is desired, it may be separated from the other isomers by fractional distillation, e.g., superfractionation, since its boiling point is sufficiently higher than the boiling point of the other $C_8$ alkyl aromatic hydrocarbons to permit effective separation by conventional distillation techniques. The remaining isomers can then be subjected to further isomerization by recycling them to the isomerization reactor. However, the meta- and para-isomers are not readily separated from each other by distillation techniques because of these isomers' boiling points. They can be separated from each other by chemical separation techniques well known to the art such as sulfuric acid sulfonation, alkylation-dealkylation techniques, etc. In addition, paraxylene may be recovered by physical separation methods such as crystallization or adsorption-desorption.

The $C_8$ alkyl aromatic hydrocarbon-containing feedstock to the process of the present invention can be substantially pure $C_8$ alkyl benzene isomer, a mixture of $C_8$ alkyl benzene isomers, or hydrocarbon fractions rich in $C_8$ alkyl benzene isomers. For example, a source of $C_8$ alkyl benzene isomers is the $C_8$ aromatic fraction recovered from catalytic reformates, pyrolysis naphthas, or coal tars. The $C_8$ alkyl benzene fraction remaining after separating and recovering all or a part of a given isomer from such a source is a suitable $C_8$ alkyl aromatic-containing feedstock for the process of the invention. Thus, paraxylene, which is of growing importance, can be recovered from a $C_8$ catalytic reformate fraction by low temperature crystallization. The mother liquor produced from such low temperature crystallization is deficient in paraxylene with respect to the thermodynamic equilibrium concentration of $C_8$ alkyl benzene isomers and is an excellent $C_8$ alkyl aromatic-containing feedstock to the present process.

As will be recognized by one skilled in the art, the process of this invention utilizing the catalyst hereinbefore set forth, may be effected in any suitable manner and may comprise either a batch or continuous operation. The preferred method by which the process of this invention may be effected is the continuous type operation. Thus, a particularly preferred method of the fixed bed operation is one in which a non-equilibrium $C_8$ alkyl aromatic hydrocarbon fraction is continuously charged to the reaction zone containing the fixed bed of the desired catalyst, the zone being maintained at the proper operating conditions of temperature and pressure as described above. The reaction zone may comprise an unpacked vessel or coil or may be lined with an adsorbent packing material.

To further illustrate the beneficial importance and effectiveness of this invention, the following examples are presented. These examples are, however, not presented for purposes of limiting the scope of this invention but in order to further illustrate the embodiments thereof.

EXAMPLES I AND II

These examples illustrate certain of the advantages of the present process.

A $C_8$ alkl aromatic isomerization system was operated to recover an orthoxylene product and a paraxylene product. The catalyst used in the isomerization reaction zone was a commercially available catalyst containing about 0.4% by weight of platinum, calculated as elemental metal, on a silica-alumina support. The catalyst was disposed in a fixed bed reaction system.

In the standard mode of operation, the isomerization system process flow was as follows: A fresh feed, non-equilibrium mixture of $C_8$ alkyl aromatics was combined with a recycle stream, described below and sent to the reaction zone where it was combined with hydrogen so that the hydrogen to $C_8$ alkyl aromatic hydrocarbon mole ratio in the feed to the reaction zone was about 8.8. The effluent from the reaction zone was sent to a flash drum to remove a hydrogen-containing gaseous material from the effluent. This hydrogen-containing stream was at least partially recycled to the reaction zone. The remainder of the effluent was sent to a first distillation tower to remove light ends from the effluent. The first distillation tower was operated, e.g., at suitable temperatures and pressures, so as to produce both a liquid overhead product and a gaseous overhead product.

In conventional operation of the isomerization system, both liquid and gaseous products from the first distillation tower were removed from the process. The bottoms product from this first distillation column was sent to further processing, e.g., further distillation to remove $C_9+$ material from the reactor effluent, superfractionation to remove an orthoxylene product and crystallization to remove a paraxylene product. The remaining material after crystallization was recycled back to the isomerization reaction zone to be combined with the fresh feed as first indicated.

The reaction conditions in the isomerization reaction zone were as follows:

| | |
|---|---|
| Hydrogen to C$_8$ Alkyl Aromatic Hydrocarbon Mole Ratio | 8.8 |
| Reactor Pressure, psig. | 203 |
| Reactor Outlet Temperature, °F. | 815 |

In the conventional operation, described above, the results across the isomerization reaction zone were as follows:

| | |
|---|---|
| C$_8$ Ring Retention, % | 96 |
| Approach to Equilibrium, %[1] | |
| Paraxylene | 88 |
| Metaxylene | 83 |
| Orthoxylene | 77 |
| Ethylbenzene | 49 |

[1] The total feedstock to the isomerization reaction zone includes a non-equilibrium mixture of C$_8$ alkyl aromatics. The isomerization in the reaction zone tends to produce an equilibrium mixture of these C$_8$ alkyl aromatics. Therefore, the greater the approach to equilibrium, i.e., higher percent approach to equilibrium, the more complete or efficient the isomerization in the reaction zone. Published equilibrium values were used in calculating the approaches to equilibrium.

In a revised operation according to the present invention, a portion, i.e., about 64% by weight, of the first distillation tower liquid overhead was routed to the reaction zone and combined with the other feed streams, described above, entering the reaction zone. This routed portion represented about 60% by weight of the total vapor and liquid products from this first distillation tower. The reaction conditions were the same as noted above. This first distillation tower liquid overhead contained about 22% by weight C$_5$− paraffins, about 10% by weight C$_6$+ paraffins, about 6% by weight C$_5$ and C$_6$ naphthenes, about 6% by weight C$_7$ naphthenes, about 4% by weight C$_8$ naphthenes, about 11% by weight benzene and about 41% by weight toluene. The recycled first distillation tower liquid overhead equalled about 1.8% of the total hydrocarbon feed to the reaction zone.

Results across the isomerization reaction zone with the operating according to the present invention were as follows:

| | |
|---|---|
| C$_8$ Ring Retention, % | 97 |
| Approach to Equilibrium, %[1] | |
| Paraxylene | 102 |
| Metaxylene | 102 |
| Orthoxylene | 102 |
| Ethylebenzene | 44 |

[1] The total feedstock to the isomerization reaction zone includes a non-equilibrium mixture of C$_8$ alkyl aromatics. The isomerization in the reaction zone tends to produce an equilibrium mixture of these C$_8$ alkyl aromatics. Therefore, the greater the approach to equilibrium, i.e., higher percent approach to equilibrium, the more complete or efficient the isomerization in the reaction zone. Published equilibrium values were used in calculating the approaches to equilibrium.

The results presented above indicate that improved yields of valuable C$_8$ alkyl benzene isomers are achieved by routing at least a portion of the liquid overhead from the first distillation tower to the isomerization reaction zone according to the present invention. For example, not only is the C$_8$ ring retention improved (relative to the conventional operation) with the revised operation, but also, and quite unexpectedly, the approaches to equilibrium of the C$_8$ dimethyl benzene isomers are substantially improved. That is, with routing of the liquid overhead from the first distillation tower to the isomerization reaction zone, the concentrations of paraxylene and orthoxylene in the effluent from the reaction zone, based on the total C$_8$ alkyl benzene content, are increased relative to the conventional operation. Therefore, improved yields of orthoxylene and paraxylene are obtained when processing to obtain such products.

The embodiments of the invention in which an exclusive property or privilege is claimed are defined as follows:

1. In a process for isomerizing a C$_8$ alkyl aromatic hydrocarbon-containing feedstock comprising the steps of (1) contacting said feedstock in at least one isomerization zone with a catalyst including at least one hydrogenation component and being effective to promote C$_8$ alkyl benzene isomerization at isomerization conditions in the presence of hydrogen at isomerization conditions to isomerize at least a portion of said C$_8$ alkyl aromatic hydrocarbons and to produce an effluent; (2) separating said effluent to form a hydrogen-rich fraction, a first hydrocarbon-rich fraction containing benzene and toluene and having a lower average molecular weight relative to C$_8$ alkyl aromatic, and a second fraction enriched in C$_8$ alkyl aromatic content relative to said effluent; and (3) recovering at least one C$_8$ alkyl aromatic product from said second fraction: the improvement which comprises subjecting at least a portion of said first hydrocarbon-rich fraction to the contacting of step (1).

2. The process of claim 1 wherein said first hydrocarbon-rich fraction is substantially free of C$_8$ alkyl aromatic hydrocarbons.

3. The process of claim 2 wherein said first hydrocarbon-rich fraction is formed in a distillation tower system operated so that at least a portion of the overhead product exits said system as a gaseous material.

4. The process of claim 3 wherein said first hydrocarbon-rich fraction subjected to the contacting of step (1) comprises at least a portion of the liquid overhead product from said tower system.

5. The process of claim 2 wherein a portion of said first hydrocarbon-rich fraction is subjected to the contacting of step (1).

6. The process of claim 5 wherein said first hydrocarbon-rich fraction further comprises C$_8$ naphthenes.

7. The process of claim 6 wherein the amount of toluene and C$_8$ naphthenes in said first hydrocarbon-rich fraction is a portion of the total toluene and C$_8$ naphthenes subjected to step (2).

8. The process of claim 7 wherein at least about 30% by weight of said first hydrocarbon-rich fraction is subjected to the contacting of step (1).

9. The process of claim 7 wherein at least about 40% by weight of said first hydrocarbon-rich fraction is subjected to the contacting of step (1).

10. The process of claim 7 wherein at least about 50% by weight of said first hydrocarbon-rich fraction is subjected to the contacting of step (1).

11. The process of claim 7 wherein said hydrogenation component is selected from the group consisting of Group VI metal components, Group VII metal components, Group VIII metal components and mixtures thereof.

12. The process of claim 11 wherein said catalyst contains at least one aluminosilicate capable of promoting C$_8$ alkyl aromatic isomerization at the conditions of step (1).

13. The process of claim 11 wherein said component is selected from the group consisting of platinum group metal component and mixtures thereof and said platinum group metal component is present in an amount of about 0.02% to about 3.0% by weight of said catalyst, calculated as elemental metal.

14. The process of claim 13 wherein said catalyst contains at least one aluminosilicate capable of promoting $C_8$ alkyl aromatic isomerization at the conditions of step (1), said aluminosilicate being present in an amount of about 1% to about 75% by weight of the total catalyst.

15. The process of claim 11 wherein said conditions of step (1) include temperatures of about 50° F. to about 1200° F.; weight hourly space velocity of about 0.1 to about 40; pressure of about atmospheric to about 100 atmospheres; and hydrogen to $C_8$ alkyl aromatic hydrocarbon mole ratio of about 0.5:1 to about 25:1.

16. The process of claim 14 wherein said conditions of step (1) include temperatures of about 400° F. to about 1000° F.; weight hourly space velocity of about 0.5 to about 8; pressure of about 5 atmospheres to about 50 atmospheres; and hydrogen to $C_8$ alkyl aromatic hydrocarbon mole ratio of about 3:1 to about 15:1, provided that the reactants in said isomerization zone are substantially vaporous.

* * * * *